United States Patent [19]

Derweduwen

[11] 4,281,649

[45] Aug. 4, 1981

[54] OSTEOSYNTHESIS METHOD AND APPARATUS FOR REDUCING A BONE FRACTURE

[76] Inventor: Joan Derweduwen, Kruisven 64, 2400 Mol, Belgium

[21] Appl. No.: 892,987

[22] Filed: Apr. 3, 1978

[30] Foreign Application Priority Data

Apr. 1, 1977 [NL] Netherlands .................. 7703616

[51] Int. Cl.³ .................. A61F 5/04; A61B 17/18
[52] U.S. Cl. .................. 128/92 BC; 128/92 A; 128/92 EB; 128/92 G
[58] Field of Search ............ 128/92 BC, 92 BB, 92 B, 128/92 A, 92 R, 92 E, 92 EB, 92 G

[56] References Cited

U.S. PATENT DOCUMENTS

| | | | |
|---|---|---|---|
| 2,821,979 | 2/1958 | Cameron | 128/92 BC |
| 3,441,017 | 4/1969 | Kaessmann | 128/92 BC |
| 3,763,855 | 10/1973 | McAtee | 128/92 BC |
| 3,765,034 | 10/1973 | Johnston | 128/92 BC X |

*Primary Examiner*—Ronald L. Frinks

*Attorney, Agent, or Firm*—Robert E. Burns; Emmanuel J. Lobato; Bruce L. Adams

[57] ABSTRACT

The osteosynthesis method in accordance with the invention renders it possible to heal bone fractures of any nature, even relatively complex ones, without plaster, without pain, without external elements and within very short periods.

This method consists in drilling a longitudinal passage 5 into the fractured bone from one of its extremities, in drilling a transverse hole 10 through each piece of bone, in inserting a peg 11, 12 in each transverse hole, in exerting on these pegs via a drawbar comprising a mandrel 17 in this instance whereof the screw-threaded extremity 18 is screwed into an internal screw thread of the peg 12 and whereof a shoulder 19 bears on a peg 13, a longitudinal force placing in intimate contact and exposing to a particular degree of compression the two surfaces of the break and in thus maintaining this compressive force until healing has occurred, then after this healing action, in removing the different parts in reverse order to that of their insertion.

19 Claims, 13 Drawing Figures

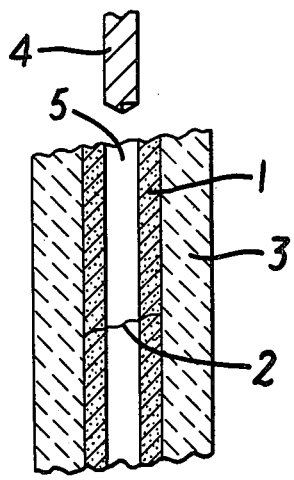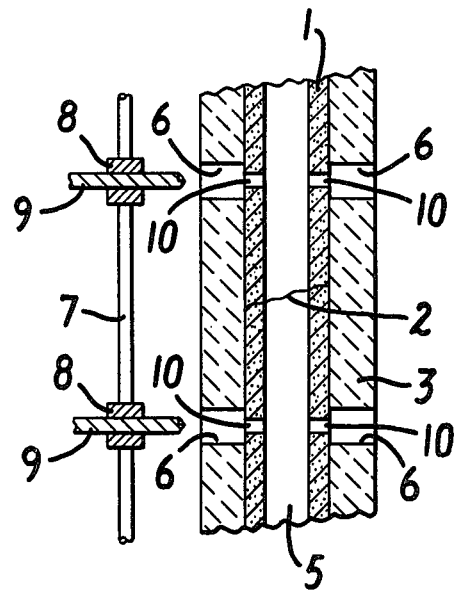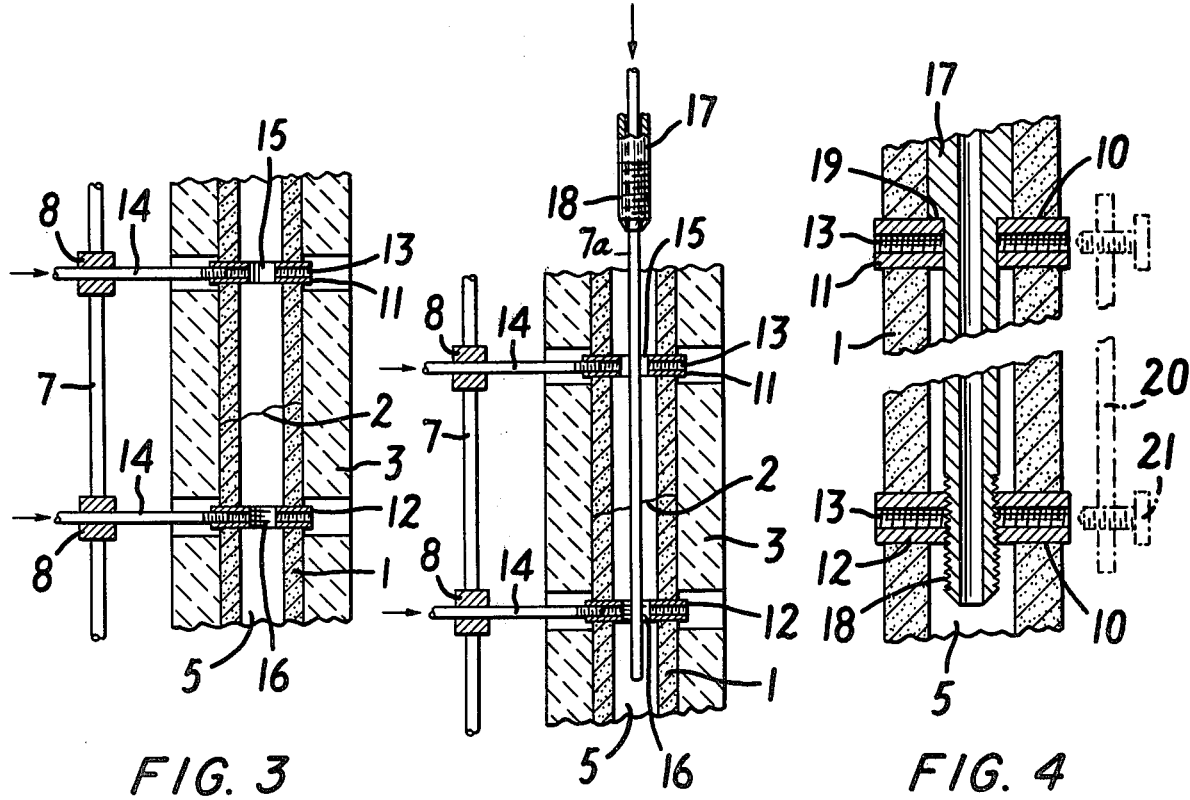
FIG. 1  FIG. 2  FIG. 3  FIG. 3a  FIG. 4

OSTEOSYNTHESIS METHOD AND APPARATUS FOR REDUCING A BONE FRACTURE

BACKGROUND OF THE INVENTION

The present invention relates to an osteosynthesis method for reducing bones fractures.

One of the best known osteosynthesis methods presently available consists in drilling the broken bone longitudinally from one of its extremities and subsequently inserting a radially extensible pin into the bore produced.

This method has several disadvantages. In the first place, the bone placed under an internal radial strain may split the bone, particularly if its strength is reduced by decalcification. In the second place, these pins cannot be used for children whose bones are as yet insufficiently hard to withstand such strains. Finally, if the break is total, the osseous fragments may be displaced axially or pivot with respect to each other, thus comprising the healing process.

A method involving the use of plate spanning the break and secured to the pieces of bone, or two plates secured at either side of the break and interconnected by one or more rods, is occassionally used to avoid these disadvantages. It is thus possible to prevent misalignment or alteration of the pieces of bone, but not a mutual deviation under the action of muscular forces or of a transverse load.

Another known osteosynthesis method consists in making a transverse perforation in the bone at either side of the break, in inserting into the perforations studs which project beyond the muscular tissue surrounding the bone and which are interconnected at both their extremities and at the outside of the limb by means of screw tensioners in such manner that the pieces are powerfully drawn together.

This method also has numerous shortcomings. Thus, the operation wounds around the studs do not heal and are prone to inflammation and infection throughout the treatment period. The external tensioners are also troublesome. Finally, it is practically impossible to tighten the tensioners in a uniform manner to obtain strict alignment of the bone pieces.

SUMMARY OF THE INVENTION

The present invention has as its object an osteosynthesis method which mitigates these drawbacks, as well as equipment for the application of this method.

The present invention provides an osteosynthesis method for reducing a bone fracture, which comprises drilling a longitudinal passage into a broken bone from an extremity thereof, forming a transverse hole through each piece of bone on opposite sides of the fracture, inserting a peg into each transverse hole, exerting a force on these pegs tending to draw the pegs together by means of a compressioning means situated within the longitudinal passage so as to bring the surfaces of the fracture into intimate contact and to hold them thus until the fracture has healed.

BRIEF DESCRIPTION OF THE DRAWINGS

The accompanying drawings illustrate embodiments of the invention by way of example, wherein:

FIG. 1 is a view in longitudinal cross-section of a broken bone; and

FIGS. 2 to 4 are cross-sectional views analogous to FIG. 1 corresponding to the consecutive operations of the method;

DESCRIPTION OF THE PREFERRED EMBODIMENTS

Figure 5:
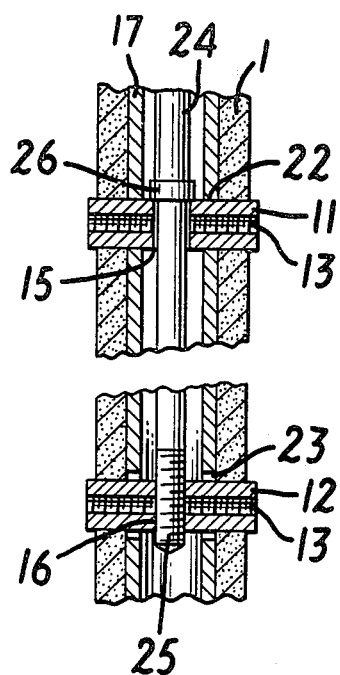
FIGS. 5 to 10 are cross-sectional views analogous to FIG. 4, illustrating modified versions and other particular applications of the method.

The first operation of the osteosynthesis method for healing the limb (FIG. 1), whereof a bone 1 surrounded by muscular tissue 3 has a fracture 2, consists in drilling a passage 5 into the bone marrow from one of the extremities of the bone by means of an auger 4.

The second operation consists in making (FIG. 2) incisions 6 in the muscular tissue 3 at either side of the fracture, and then drilling transverse holes 10 through the bone 1 and the passage 5 with drills 9 by means of a jig 7 comprising two parallel guiding sleeves 8.

After removing the drills 9, the third operation consists in inserting two tubular pegs 11 and 12 each equipped with a tapping 13 into the holes 10 by means of screw-threaded rods 14 which are screwed into the tappings 13 and which are guided by the sleeves 8.

The pegs 11 and 12 each have a transverse bore 15 and 16 respectively, the latter being tapped. Their lengths are a little greater than the diameter of the bone abreast of the holes 10 and their bores are aligned in the axis of the passage 5.

The fourth operation consists of inserting into the passage 5 (FIG. 4) a mandrel 17 equipped at its extremity with a screw thread 18 which passes freely through the bore 15 and is screwed into the tapped bore 16. This mandrel 17 has a shoulder 19 which bears on the rim of the bore 15. By screwing this mandrel, the pegs are pulled towards each other, thus forcing the bone pieces against each other.

The mandrel 17 may also comprise a nut adapted to bear against the second peg. Also, the scew-thread of the extremity of mandrel 17 and a screw thread on the mandrel 17 cooperating with the nut are contra-directionally threaded.

This operation is obviously monitored by radiography apparatus. The rods 14 are removed and the operation wounds are closed again, being sutured if appropriate, the fracture having been reduced perfectly and the pieces of bone being in intimate contact with each other.

The fracture is kept under axial compression and is thus consolidated very quickly without pain and the adjacent muscles very quickly become usable again. The broken limb may also regain a degree of mobility prior to healing, in the absence of any plaster sheathing, or even a certain degree of activity. It may even bear certain loads without risk of deviation of the bone pieces.

The different components are removed consecutively, in reverse order, when the break has healed. Use is again made of the jig 7, the sleeves 8 and the screw-threaded rods 14, to extract the pegs 11 and 12. Auxiliary plates 20 equipped with bolts 21 (shown dash-dotted in FIG. 4) which are screwed into the tappings 13 may be installed on the pegs 11 and 12, in the case of fractures in which there is a risk of slipping.

The jig 7 may be constructed in such manner that the spacing between the sleeves 8 is adjustable. As shown in FIG 3a, prior to inserting the mandrel 17, it may be advantageous to insert a guiding wire or rod 7a through the passage 5 and the holes 15 and 16, to locate the precise position of these holes.

Use may also be made of a guiding rod whereof the screw-threaded extremity is screwed into the hole 16.

In the version illustrated in FIG. 5, a view analoguous to FIG. 4, the mandrel 17 has transverse openings 22 and 23, the second being greater than the first, which are traversed by the pegs 11 and 12. The reduction of the fracture and the compressioning of the pegs 11 and 12 are achieved by means of a clamping rod 24, whereof the screw-threaded extremity 25 is screwed into the tapped bore 16 and which has a collar 26 bearing against the peg 11.

Figure 5A:
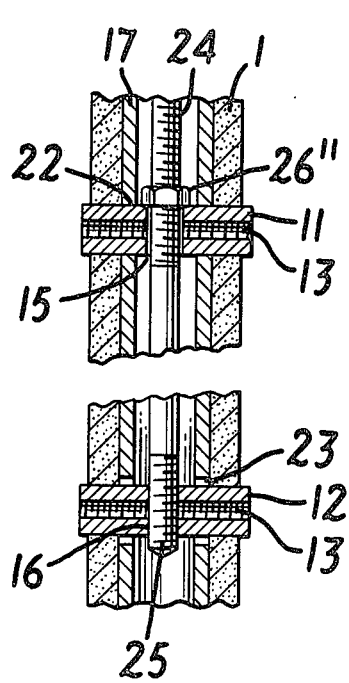

The collar 26 may be replaced by a nut 26'', illustrated in FIG. 5a whose internal screw thread is opposed in direction to that of the extremity 25 in such manner that the pegs 11 and 12 are caused to approach each other upon screwing-up the rod 24.

Figure 6:
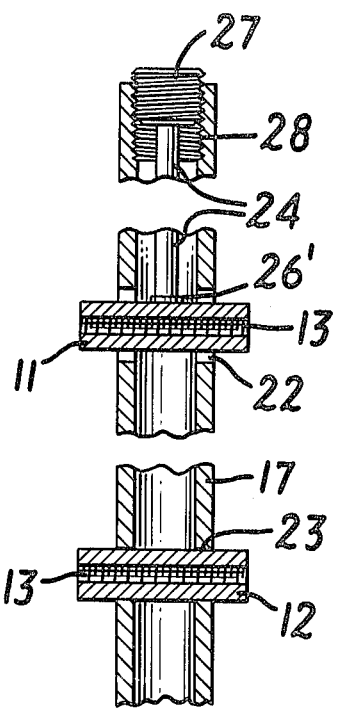

In the version illustrated in FIG. 6, the opening 22 is wider than the peg 11, whereas the opening 23 corresponds to the diameter of the peg 12.

The compressioning action is obtained by causing the rotation of an element formed by a rod 24 bearing via its lower extremity 26' against the peg 11 and of a screw-threaded head 27 screwed into a tapping 28 of the upper extremity of the mandrel 17.

Figure 7:
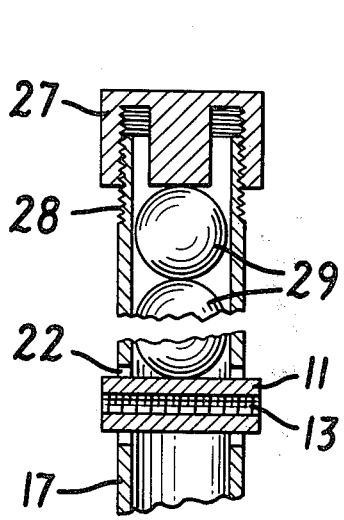

In the version illustrated in FIG. 7, the rod 24 is replaced by spheroids 29 and the head 27 by a screw-threaded plug 27.

Figure 8:
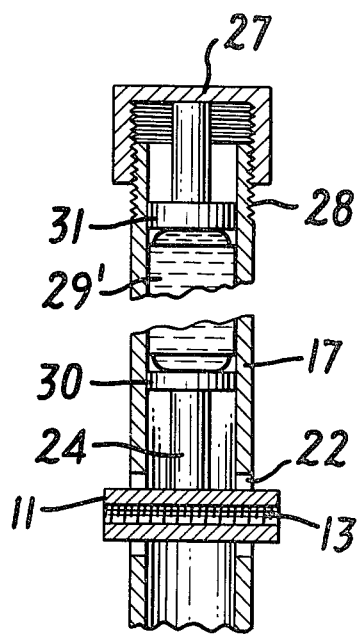
Figure 9:
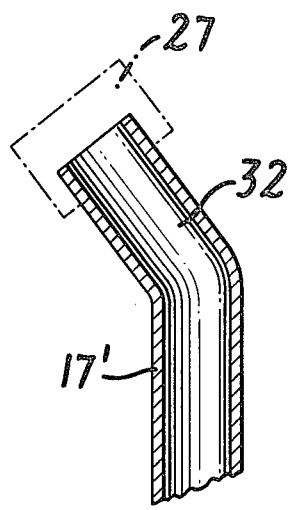

In the version illustrated in FIG. 8, the connection between the peg 11 and the plug 27 is assured by means of a flexible sheath containing a liquid 29', enclosed between two pistons 30 and 31. These last two versions are particularly advantageous in all cases in which use has to be made of a cranked mandrel 17'.

The balls 29 or the liquid 29' may be inserted via the elbow 32 and the compressive force may be transmitted via this elbow through a flexible rod 24 or a coil spring.

Provision may be made moreover for the use of pegs of rectangular cross-section, which do not transverse the passage 5, in the versions of FIGS. 6 to 8.

The process in accordance with the present invention is particularly appropriate for treating and healing serious complex fractures very rapidly.

Figure 10:
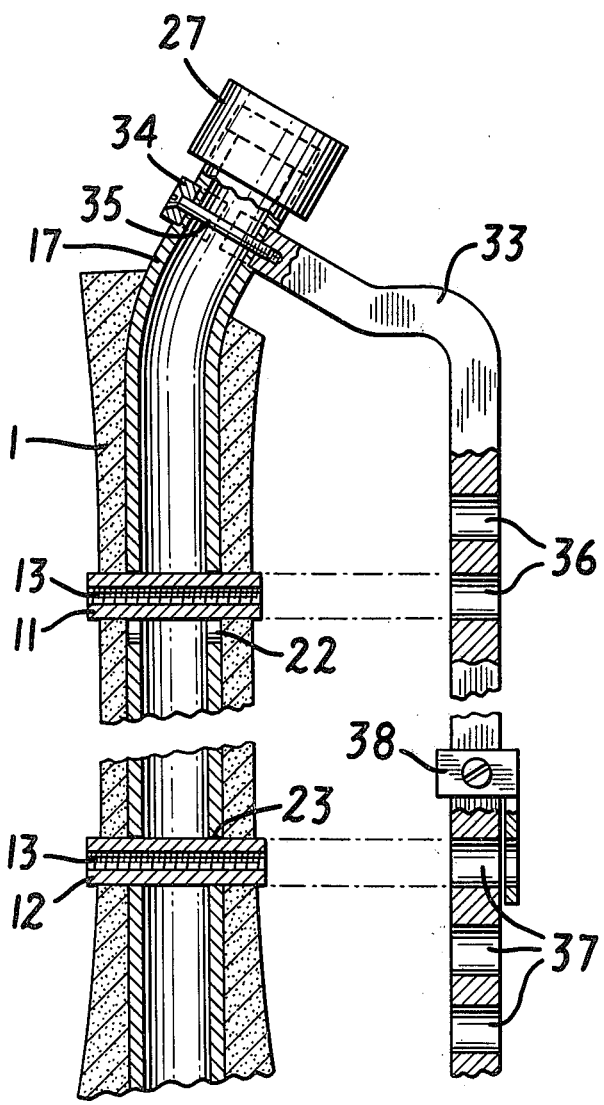
Figure 11:
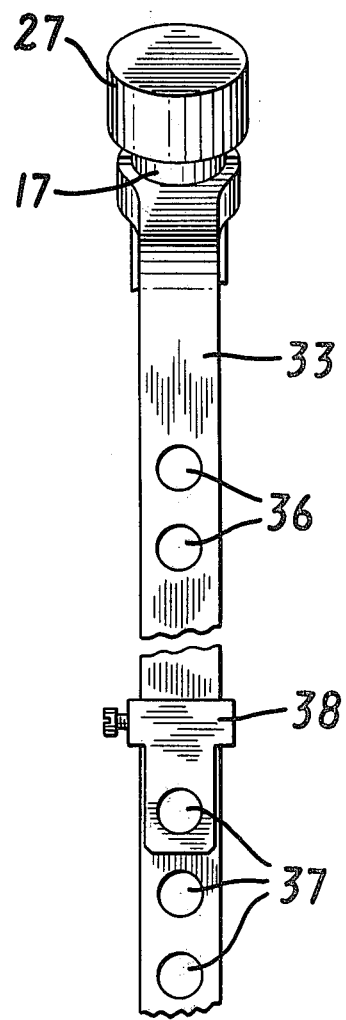
FIG. 11 is a side view corresponding to FIG. 10.

A version of the form of embodiment illustrated in FIG. 6 has also been illustrated in FIGS. 10 and 11. This version comprises a drilling jig 33 which is removably secured on the bent upper extremity of the mandrel 17 by means of a fastening collar 34 and locking screw 35.

This jig 33 has two holes 36 and a series of holes 37 for guiding augers intended for drilling holes into the pieces of bone abreast of the openings 22 and 23 of the mandrel 17. One of the two holes 36 and one of the holes 37 are aligned precisely with the upper opening 22 of the mandrel 17 (or, more precisely, with the upper part of this opening to allow of the peg 11 being displaced downwards) and the lower opening 23. A cursor 38 sliding along the jig and which may be immobilised by means of a screw, renders it possible to mark the hole 37 corresponding to the opening 23 in such manner that after insertion of the mandrel 17 into the bone, the operating surgeon has no hesitation with regard to the hole 37 to be used for piercing the bone at the level of this opening.

The unused holes 36 and 37 are incorporated for other mandrels 17 in which the openings 22 and 23 have different spacings.

I claim:

1. An osteosynthesis method for reducing a bone fracture, which comprises drilling a longitudinal passage into a broken bone from an extremity thereof, forming a transverse hole through each piece of bone on opposite sides of the fracture, inserting a peg into each transverse hole, exerting a force on these pegs tending to draw the pegs together by means of a compressioning means situated within the longitudinal passage so as to bring the surfaces of the fracture into intimate contact and to hold them thus until the fracture has healed.

2. A method according to claim 1, wherein the transverse holes are drilled with the aid of a jig for guiding tools drilling the transverse holes in the pieces of bone.

3. A method according to claim 1 or 2, wherein a jig is also used for removal of the pegs after healing.

4. Apparatus for reducing a bone fracture which comprises first and second pegs intended to be placed in spaced transverse holes in respective bone fragments and compressioning means intended to be inserted into a passage drilled longitudinally into the broken bone so as to place the pegs under compression, wherein said compressioning means comprises a screw threaded mandrel adapted to be screwed into a tapped bore of one of the pegs while bearing against a second peg by means of a shoulder.

5. Apparatus for reducing a bone fracture which comprises first and second pegs intended to be placed in spaced transverse holes in respective bone fragments and compressioning means intended to be inserted into a passage drilled longitudinally into the broken bone so as to place the pegs under compression, wherein said compressioning means comprises a screw threaded mandrel adapted to be screwed into a tapped bore of one of the pegs while bearing against a second peg by means of a nut.

6. Apparatus according to claim 5, wherein the screw-thread of the mandrel extremity and a screw thread on the mandrel cooperating with the nut are contra-directionally threaded.

7. Apparatus for reducing a bone fracture which comprises first and second pegs intended to be placed in spaced transverse holes in respective bone fragments and compressioning means intended to be inserted into a passage drilled longitudianally into the broken bone so as to place the pegs under compression, wherein the compressioning means comprises a hollow mandrel and a rod positioned coaxially with respect to the tubular mandrel and co-operating with the pegs.

8. Apparatus according to claim 7, wherein the rod is screw-threaded and is adapted to be screwed into a tapped bore in one of the pegs whilst bearing against the second peg.

9. Apparatus for reducing a bone fracture which comprises first and second pegs intended to be placed in spaced transverse holes in respective bone fragments and compressioning means intended to be inserted into a passage drilled longitudinally into the broken bone so as to place the pegs under compression, wherein the compressioning means comprises a mandrel and at least one intermediate element for situation between a screw-threaded or tapped element screwed on the said mandrel, and one of the two pegs.

10. Apparatus according to claim 9, wherein said intermediate element is a rod.

11. Apparatus according to claim 9, wherein said elements are spheroids.

12. Apparatus according to claim 9, wherein said intermediate elements are two pistons between which is situated a deformable substance.

13. Apparatus according to claim 9, which further comprises a jig having at least two guiding sleeves.

14. Apparatus according to claim 13, wherein the spacing of said sleeves is adjustable.

15. Apparatus according to claim 13, wherein said sleeves are tapped.

16. Apparatus for reducing a bone fracture which comprises first and second pegs intended to be placed in spaced transverse holes in respective bone fragments and compressioning means intended to be inserted into a passage drilled longitudinally into the broken bone so as to place the pegs under compression, wherein said compressioning means comprises a hollow mandrel which is cranked.

17. Apparatus according to claim 16, which further comprises extension rods adapted to be coupled to the pegs.

18. Apparatus for reducing a bone fracture which comprises first and second pegs intended to be placed in spaced transverse holes in respective bone fragments; compressioning means intended to be inserted into a passage drilled longitudinally into the broken bone so as to place the pegs under compression, wherein said compressioning means comprises a hollow mandrel having openings for transversal by pegs; and a drilling jig adapted to be secured removably on the extremity of the mandrel, and having two series of guiding holes, the first aligned precisely with upper transverse openings made in the mandrel and the second aligned precisely with lower openings in the mandrel into which the pegs should be inserted and wherein the jig comprises means of marking at least one of the two drilled holes corresponding to the openings of the mandrel.

19. Apparatus according to claim 18, wherein said marking means comprise a cursor.

* * * * *